United States Patent [19]

Nitschmann et al.

[11] 3,984,391

[45] Oct. 5, 1976

[54] MODIFIED GELATIN WITH A REDUCED GEL-MELTING POINT

[75] Inventors: Hans Nitschmann, Bern; Hans-Rudolf Stoll, Rufenacht; Andreas Gardi, Uettligen, all of Switzerland

[73] Assignee: Laboratorien Hausmann AG, St. Gallen, Switzerland

[22] Filed: Sept. 25, 1974

[21] Appl. No.: 509,213

[30] Foreign Application Priority Data

Sept. 26, 1973 Germany............................ 2348294

[52] U.S. Cl................................ 260/117; 424/101
[51] Int. Cl.$^2$............................................ C09H 1/00
[58] Field of Search .................................... 260/117

[56] References Cited

UNITED STATES PATENTS

| 2,413,815 | 1/1947 | Epstein ............................... 260/117 |
| 2,834,683 | 5/1958 | Corben et al. ...................... 260/117 |
| 3,057,782 | 10/1962 | Lindner et al. ..................... 260/117 |
| 3,763,138 | 10/1973 | Rakoczy ............................ 260/117 |
| 3,778,278 | 12/1973 | Rakoczy ............................ 260/117 |

*Primary Examiner*—Lewis T. Jacobs
*Assistant Examiner*—H. H. Fletcher
*Attorney, Agent, or Firm*—Donald D. Jeffery

[57] ABSTRACT

The invention relates to a modified gelatin with a reduced gel-melting point. The gel-melting point of the modified gelatin is reduced by converting at least 6% of the optically active amino acid residues in the gelation from this original L-form to D-form.

29 Claims, No Drawings

MODIFIED GELATIN WITH A REDUCED GEL-MELTING POINT

This invention relates to a modified gelatin with a reduced gel-melting point and an average molecular weight of at least about 20,000, and to a process for its production.

BACKGROUND OF INVENTION

Gelatins and chemically modified gelatins are widely used for a variety of commercial purposes. Gel formation is essential to almost all commercial applications involving gelatin, occurring when the aqueous solutions prepared under moderate heat are cooled. A gelatin normally counts as "good" when the melting point of the gel, for a given concentration, is relatively high and when the gel is mechanically solid. However, there are applications where gelation is either unnecessary or even undesirable. One example of this type of application is the use of the gelatin as a colloid in plasma substitutes or transfusion solutions of the kind used clinically, for example, for treating shock. Solutions of this kind, containing approximately 3 to 5% of gelatin, should remain liquid at temperatures down to around 0°C. An approximately 4% solution of a standard commercial-grade gelatin with an average molecular weight ($M_n$) of from 30,000 to 70,000 gels at temperatures of from 24° to 32°C and, for this reason, is not suitable for direct use as a colloid in a blood plasma substitute.

Although the gel-melting point can be reduced to almost any extent by hydrolytically degrading gelatin, i.e. by reducing the average molecular weight, this does not apply to gelatin of the kind used for transfusion purposes, because the colloid leaves the circuit more quickly, the smaller the molecules.

Accordingly, attempts have been made to modify gelatin chemically in such a way that gelability (as measured from the gel-melting point) is drastically reduced for a given average molecular weight. In this connection, it is known that gelatin can be simultaneously degraded and crosslinked, branched or, in some cases, even inner-molecularly bridged molecules can be formed from the linear gelatin molecules. Although the average molecular weight can be kept at a relatively high level, the average free (unbranched) chain length becomes shorter. This complicates reformation of the helical conformation typical of collagen and gelatin which is a prerequisite for gelatin.

SUMMARY OF INVENTION

The object of the present invention is to obtain a modified gelatin with a gel-melting point considerably lower than that of a standard gelatin of the same average molecular weight, by a totally different method and without the incorporation of foreign molecules which is what the crosslinking reagents represent.

The invention relates to a modified gelatin with a reduced gel-melting point and an average molecular weight of at least about 20,000, which is distinguished by the face that at least 6% of the sum total of the optically active amino acid residues, present in the gelatin, of alanine, isoleucine, leucine, serine and proline are present in the D-form.

In native collagen, all the amino acid residues are present in the L-configuration. D-amino acid residues can only be detected in traces in standard commercial-grade gelatins which have been obtained by boiling collagen pretreated with lime or with acid. It has now been found that the gelatin according to the invention, in which some of the amino acid residues are present in the D-form, have a considerably lower gel-melting point than a corresponding native gelatin in which almost all the amino acid residues are present in the L-configuration, although the gelatin according to the invention has the same chain length as, or only a slightly shorter chain length than, the corresponding native gelatin. According to the invention, therefore, the gelatin obtained is uncrosslinked and has a relatively high molecular weight and a low gel-melting point. The reduction in the gel-melting point is greater, the greater the proportion of amino acid residues present in D-form in the gelatin. The gelatin according to the invention is prepared by converting at least 6% of the sum total of the optically active amino acid residues, present in the gelatin, of alanine, isoleucine, leucine, serine and profine into the D-form. The optically active amino acid residues are converted into the D-form by heating the gelatin at a pH-value of at least 10.5, preferably in the range from 11 to 11.5, as measured at 90°C, to temperatures in the range from 90° to 160°C, preferably to temperatures in the range from 130° to 160°C, until the required degree of racemisation is obtained, subsequently stopping the reaction suddenly by reducing the pH-value and/or by reducing the temperature, optionally removing inorganic salts from the solution and recovering the modified gelatin. The required degree of racemisation is governed by the purpose for which it is intended to use the gelatin. Gelatin with a molecular weight of about 20,000 actually has a gel-melting point of around 0°C when only about 6% of the sum total of the optically active amino acid residues present in the gelatin, of alanine, isoleucine, leucine, serine and proline are present in the D-form and when the aqueous gelatine solution has concentration of around 4% by weight. In cases where it is intended to prepare solutions with the same concentration from a gelatin with a higher average molecular weight, with a gel-melting point of around 0°C, the proportion of amino acid residues present in the D-form must be correspondingly higher, preferably at least 8% and, with particular preference, at least 10%.

Aqueous solutions with a concentration of from 3 to 6% by weight, preferably from 3.5 to 4.5% by weight, of gelatin are preferably used as blood plasma substitute. For this purpose, it is preferred in accordance with the invention to use a gelatin with an average molecular weight of at least about 24,000, preferably from 25,000 to 30,000 or, in some cases, from more than 30,000 to around 60,000. In a gelatin of this kind according to the invention, approximately 10 to 12% of the optically active amino acid residues, present in it, of alanine, isoleucine, leucine, serine and proline, are present in the D-form. In cases where it is desired to obtain a gelatin according to the invention which has an even higher molecular weight and a gel-melting point of around 0°C in the form of an approximately 4% by weight aqueous solution, the proportion of the aforementioned amino acid residues present in the D-form should with advantage amount to at least 12%. More than 25% and up to 50% can be present in the D-form.

The gel-melting point is determined by 0. Gerngross' method (Z. angew. Chemie 42, 971 (1929), modified by H. R. Stoll (Diss. Bern, 1967).

The average molecular weight ($M_n$) is determined osmometrically in accordance with Nitschmann et al., Vox sang 12, 106 (1967).

Preferred staring materials for use in the preparation of the gelatin according to the invention are the standard commercial grade gelatins emanating from mammals, for example the gelatins obtained from bovine or bones and from pigskin or bones. It is also possible to use gelatins obtained from fishskin. Since there is a certain reduction in molecular weight as a result of hydrolysis during production of the gelatin according to the invention, the gelatine used as starting product must have a correspondingly higher molecular weight than is required for the gelatin according to the invention.

In order to promote racemisation over hydrolytic degradation in the alkaline medium, it has proved to be of advantage to adjust to an extremely high pH-value in the aqueous gelatin solution by the addition of a strong base, followed by brief heating to relatively high temperatures (80°–160°C). Since the heating time has a greater influence upon increased degradation of the gelatin than the heating temperature, it is preferred to select a relatively high temperature and to keep the heating time as short as possible. The heating time required to obtain any required degree of racemisation is shorter, the higher the temperature applied. Where the temperatures specified above are applied, the required degree of racemisation is generally obtained after heating for a period of, for example, from 10 seconds to 5 minutes. In each individual case, the necessary heating time can readily be determined by a preliminary test, taking into account the required degree of racemisation, the temperature applied and the pH-value applied. In every case, it is desirable, as already mentioned, to keep the heating time as short as possible by applying a high temperature and a high pH-value, the upper limit being that at which undesirable decomposition or undesirable degradation of the gelatin is avoided. The reaction can be stopped by neutralisation with an acid, followed or accompanied by cooling, or by extremely rapid cooling, followed by neutralisation.

It is also possible to work in a non-aqueous solvent, (in the absence of water) such as dimethylsulfoxide, in which case it is of advantage to use such bases as sodium-tert-butanolate which, for steric reasons, cannot attack the peptide bond.

The brief heating of strongly alkaline, aqueous gelatin solutions can be carried out by the so-called batch process, in which case provision must be made for rapid heating and cooling, especially in the case of large batches. However, heating can also be carried out without interruption, for example by the continuous process, with which it is easier to keep strictly to the time limits for the brief heating of the alkaline solutions. Apparatus of the kind used, for example, in the food industry for uperisation (ultra-pasteurization), are suitable for procedures of this kind.

Whether and to what extent racemisation has taken place can be determined by known methods of quantitative amino acid analysis of gelatin preparations. Thus, the degree of racemisation in preparations can be determined, for example, by the gas chromatographic method developed by W. Parr et al. (J. Chromatogr. Sci. 9, 141 (1971). The process according to the invention also produces a reduction in the 4-hydroxyproline content also takes place in addition to racemisation.

Naturally gelatins degraded in this way through racemisation can be chemically further modified (for example by succinylation or by covalent crosslinking) without any change in the degree of racemisation or its effect in impairing gelability. This further chemical modification (for example acylation) may optionally be carried out at the same time as the strongly alkaline, racemising degradation. It is also possible to carry out racemisation by strongly alkaline medium on already chemically modified (for example acylated) gelatins, as already described.

Depending upon the purpose for which the partially racemised gelatin is to be used, the preparations have to be freed from the relatively high salt content left after neutralisation. Purification of the gelatin according to the invention can be carried out in known manner, for example by dialysis, by ion-exchanger resins or by precipitation. If it is to be used as a blood substitute it may be necessary to add small quantities of inorganic salts, as known to the expert. The finished solutions can be disinfected in the usual way, bottled and sterilised. These solutions can be stored for prolonged periods. However, it is also possible to prepare gelatin according to the invention from these solutions in the form of a dry preparation by applying conventional drying techniques, for example freeze-drying or spray-drying. The dry preparation obtained in this way can be redissolved at some later stage.

DESCRIPTION OF PREFERRED EMBODIMENTS

The invention is illustrated by the following Examples.

EXAMPLE 1

428g of standard commercial-grade hide or bone gelatin with an average molecular weight $M_n$ of about 45,000 are dissolved in 4.57 liters of distilled water, and the resulting solution heated to 90°C. 142 ml of 5 n NaOH are then added all at once while stirring. The pH-value rises to 10.5–11.5. After exactly 2.5 minutes, 110 ml of 5 n HCl are added, the pH-value falling to 7.5–8.0; 9.3g. of succinic acid anhydride are then added with stirring at 90°C. After 5 minutes the pH-value is adjusted to 7.0 and the solution heated for 20 minutes to 120°C in a sealed vessel. After cooling to around 60°C, the solution is completely desalted over Dowex 50 W and 21 K (or by inverse osmosis or by dialysis), and diluted to a gelatin content of 4.2%. A physiological salt content (0.9% of NaCl or Ringer lactate) is then adjusted and the pH-value adjusted to 7.1. After the solution has been filtered to remove germs, it is bottled and sterilised by heating for 20 minutes to 120°C.

The gelatin has an average molecular weight $M_n$ of 23,000. The gel-melting point of the supercooled 4% solution is 0°C. The solution has a reduced viscosity ($\eta_{rel}/c$) at 37°C of 0.24 ($\eta_{rel}$ measured at 1% gelatin concentration and 0.9% NaCl). 5.4% of the alanine, 45.8% of the isoleucine, 8.7% of the leucine, 32.4% of the serine and 7.0% of the proline are present in the D-form. If a dry form is preferred the solution is subjected immediately after filtration to remove germs to any of the conventional drying techniques (freeze-drying, spray-drying). The dry product can be dissolved in distilled water, bottled and sterilised by heating for 20 minutes to 120°C.

EXAMPLE 2

A gelatin solution with the same concentration as in Example 1 is pumped continuously through a uperising (ultra-pasteurizing) unit in which 26.8 ml of 5 n NaOH/liter are continuously added to it and in which it is heated for 30 to 60 seconds to a temperature of from 140° to 159°C. Immediately afterwards the solution is cooled by expansion to around 50°C, and neutralised by the continuous addition of 5 n HCl.

The effluent solution is completely desalted over Dowex 50 W and 21 K (or by inverse osmosis), diluted to a gelatin content of 4.2% and physiological quantities of salt (0.9% of NaCl or Ringer lactate) added. After adjustment of the pH-value to 7.1, the solution is filtered to remove germs, bottled and sterilised by heating for 20 minutes to 120°C. Data: $M_n = 25,000$; gel-melting point = 2°–3°C, reduced viscosity $(\eta_{rel}/c) = 0.27$. 9.0% of the alanine, 44.0% of the isoleucine, 9.8% of the leucine, 46.3% of the serine and 6.0% of the proline are present in the D-form.

What is claimed is:

1. A modified gelatin having a reduced gel-melting point, comprising a gelatin having an average molecular weight ($M_n$) of at least about 20,000 and having at least 6% of the sum total of the optically active amino acid residues comprising alanine, isoleucine, leucine, serine and proline present in the gelatin, present in the D-form.

2. The modified gelatin as defined by claim 1, wherein at least 8% of the sum total of said optically active amino acid residues present in the gelatin are present in the D-form.

3. The modified gelatin as defined by claim 1, wherein at least 10% of the sum total of said optically active amino acid residues present in the gelatin are present in the D-form.

4. The modified gelatin as defined by claim 1, wherein at least 12% of the sum total of said optically active amino acid residues present in the gelatin are present in the D-form.

5. The modified gelatin as defined by claim 1, wherein said average molecular weight is about 24,000.

6. The modified gelatin as defined by claim 1, wherein said average molecular weight is between about 25,000 and 30,000.

7. The modified gelatin as defined by claim 1, further characterized as being acylated.

8. The modified gelatin as defined by claim 7, wherein said modified gelatin is succinylated.

9. The modified gelatin as defined by claim 7, wherein at least 8% of the sum total of said optically active amino acid residues present in the gelatin are present in the D-form.

10. The modified gelatin as defined by claim 7, wherein at least 10% of the sum total of said optically active amino acid residues present in the gelatin are present in the D-form.

11. The modified gelatin as defined by claim 7, wherein at least 12% of the sum total of said optically active amino acid residues present in the gelatin are present in the D-form.

12. The modified gelatin as defined by claim 7, wherein said average molecular weight is at least 24,000.

13. The modified gelatin as defined by claim 7, wherein said average molecular weight is between about 25,000 and 30,000.

14. An aqueous gelatin solution comprising from about 3 to 6% by weight of the modified gelatin as defined by claim 1.

15. The solution as defined by claim 14, wherein said modified gelatin is present in an amount of from about 3.5 to 4.5% by weight.

16. An aqueous gelatin solution comprising from about 3 to 6% by weight of the modified gelatin as defined by claim 7.

17. The solution as defined by claim 16, wherein said modified gelatin is present in an amount of from about 3.5 to 4.5% by weight.

18. A process for the production of modified gelatin having a reduced gel-melting point and an average molecular weight ($M_n$) of at least about 20,000, comprising heating a normal gelatin having an average molecular weight ($M_n$) greater than about 20,000 at a strongly basic pH until at least 6% of the sum total of the optically active amino acid residues of alanine, isoleucine, leucine, serine and proline present in the gelatin have been converted into the D-form.

19. The process as defined by claim 18, wherein said normal gelatin is heated at a pH-value of at least about 10.5, as measured at 90°C, and at a temperature in the range of from about 90° to 160°C, until the required degree of racemisation has been obtained.

20. The process as defined by claim 19, wherein said pH is between about 11 and 11.5 and said temperature is between about 130° to 160°C.

21. The process as claimed in claim 19, wherein heating is carried out over a period of from 10 seconds to 5 minutes.

22. The process as defined by claim 20, wherein the process is carried out continuously.

23. The process as defined by claim 19, further comprising the steps of stopping said racemisation after the desired conversion is obtained, removing any inorganic salts present in said gelatin and recovering said modified gelatin.

24. The process as defined by claim 18, wherein said normal gelatin is acylated prior to said heating step.

25. The process as defined by claim 18, further comprising the step of reacting said normal gelatin with an acylating agent during said heating step.

26. The process as defined by claim 18, further comprising the step of reacting said modified gelatin with an acylating agent subsequent to said heating step.

27. The process as defined by claim 26, wherein said acylating agent is succinic acid anhydride.

28. An aqueous solution suitable for use as a blood plasma substitute, comprising an aqueous solution of the modified gelatin as defined by claim 1.

29. An aqueous solution suitable for use as a blood plasma substitute, comprising an aqueous solution of the modified acylated gelatin as defined by claim 7.

* * * * *